United States Patent
Shan

(10) Patent No.: US 8,404,614 B2
(45) Date of Patent: Mar. 26, 2013

(54) OXIDATION CATALYST FOR MALEIC ANHYDRIDE PRODUCTION

(75) Inventor: Zhiping Shan, The Woodlands, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 283 days.

(21) Appl. No.: 12/682,494

(22) PCT Filed: Oct. 22, 2008

(86) PCT No.: PCT/US2008/080681
§ 371 (c)(1), (2), (4) Date: Apr. 9, 2010

(87) PCT Pub. No.: WO2009/055406
PCT Pub. Date: Apr. 30, 2009

(65) Prior Publication Data
US 2010/0210858 A1 Aug. 19, 2010

Related U.S. Application Data

(60) Provisional application No. 60/981,598, filed on Oct. 22, 2007.

(51) Int. Cl.
*B01J 27/00* (2006.01)
*B01J 27/198* (2006.01)
*B01J 21/00* (2006.01)
*C07C 27/10* (2006.01)
*C07B 41/00* (2006.01)
*C07D 307/36* (2006.01)

(52) U.S. Cl. ........ 502/208; 502/209; 502/253; 568/956; 549/262

(58) Field of Classification Search .................. 502/208, 502/209, 253; 568/956; 549/262
See application file for complete search history.

(56) References Cited

U.S. PATENT DOCUMENTS

| | | | |
|---|---|---|---|
| 4,132,670 A | 1/1979 | Katsumoto et al. | |
| 4,392,986 A * | 7/1983 | Yang et al. | 502/209 |
| 4,435,521 A * | 3/1984 | Yang et al. | 502/209 |
| 4,567,158 A | 1/1986 | Wrobleski et al. | |
| 4,569,925 A * | 2/1986 | Yang et al. | 502/209 |
| 4,933,312 A * | 6/1990 | Haddad et al. | 502/209 |
| 4,996,179 A | 2/1991 | Haddad et al. | |
| 5,137,860 A | 8/1992 | Ebner et al. | |
| 5,158,923 A | 10/1992 | Barone | |
| 5,168,090 A | 12/1992 | Ebner et al. | |
| 5,275,996 A | 1/1994 | Andrews et al. | |
| 5,506,187 A | 4/1996 | Haddad et al. | |
| 5,521,134 A * | 5/1996 | Bortinger et al. | 502/39 |
| 5,530,144 A | 6/1996 | Tsurita et al. | |
| 5,773,382 A | 6/1998 | Mitchell et al. | |
| 5,792,722 A | 8/1998 | Haddad et al. | |
| 5,885,919 A | 3/1999 | Bortinger | |
| 6,174,833 B1 | 1/2001 | Bertola et al. | |
| 6,762,146 B2 | 7/2004 | Kamiya et al. | |
| 6,774,081 B1 * | 8/2004 | Datta et al. | 502/208 |
| 6,903,047 B2 | 6/2005 | Kourtakis et al. | |
| 6,956,004 B2 | 10/2005 | Albonetti et al. | |
| 7,060,649 B2 | 6/2006 | Weiguny et al. | |
| 8,143,461 B2 * | 3/2012 | Forkner | 568/956 |
| 2011/0201830 A1 * | 8/2011 | Shan | 549/257 |

* cited by examiner

*Primary Examiner* — Patricia L Hailey
(74) *Attorney, Agent, or Firm* — Huntsman International LLC

(57) ABSTRACT

A process for preparing a catalyst by selecting an active catalyst and contacting the active catalyst with one or more fluids containing an organic solvent or mixture of organic solvents. In one embodiment, each organic solvent has a dielectric constant within a range of about 5 to about 55 when measured at a temperature of 20° C. to 25° C. The catalyst thus prepared may be used in a process for preparing maleic anhydride.

19 Claims, No Drawings

OXIDATION CATALYST FOR MALEIC ANHYDRIDE PRODUCTION

CROSS-REFERENCE TO RELATED APPLICATIONS

This application is a National Stage of PCT/US08/80681, filed Oct. 22, 2008 which claims priority to U.S. Pat. App. Ser. No. 60/981,598, filed on Oct. 22, 2007 which is incorporated herein by reference.

STATEMENT REGARDING FEDERALLY SPONSORED RESEARCH OR DEVELOPMENT

Not applicable.

FIELD OF THE INVENTION

The present invention relates to a process for preparing a catalyst containing vanadium phosphorus and oxygen, to a vanadium phosphorus oxygen containing catalyst which is obtainable by the process of this invention, and to a process for preparing maleic anhydride by oxidation of hydrocarbons having at least four carbons in a straight chain or cyclic ring in the presence of such catalyst.

BACKGROUND OF THE INVENTION

Maleic anhydride may be used as a raw material in the production of many products, such as synthetic resins, and may generally be prepared by the catalytic oxidation of n-butane. The catalyst of choice for this oxidation is typically a catalyst containing vanadium, phosphorus, oxygen (VPO) and optionally a promoter component.

These catalysts are generally prepared by contacting vanadium-containing compounds with phosphorus-containing compounds and optionally promoter component containing-compounds under conditions suitable to reduce the pentavalent vanadium to the tetravalent state to thereby form a catalyst precursor containing vanadyl hydrogen phosphate and optionally the promoter component. The catalyst precursor may then be recovered and typically formed into a shaped body, such as a tablet or pellet, by compression in a die. A lubricant is ordinarily incorporated as well to aid in the tableting or pelleting process. The pellet or tablet may then be subjected to calcination to transform the catalyst precursor into an active catalyst.

Variants and different embodiments of the preparation of the active catalyst are further described in, for example: U.S. Pat. No. 4,567,158, which discloses preparation of the catalyst precursor in the presence of an alcohol-modifying agent to form a highly porous catalyst precursor which is then converted to the active catalyst; U.S. Pat. No. 4,996,179 which discloses forming the catalyst precursor into a geometric shape and calcining the shaped catalyst in an inert atmosphere at a temperature within the range of about 343° C. to 704° C. and further at an increased temperature in an oxygenous atmosphere to produce the active catalyst; U.S. Pat. No. 5,137,860 which discloses the use of three heating stages for converting the catalyst precursor into an active catalyst; U.S. Pat. No. 5,506,187 which discloses preparation of the catalyst precursor in the presence of a glycol ether solvent; U.S. Pat. No. 5,530,144 which discloses the use of orthophosphoric acid as the phosphorus-containing compound for producing the catalyst precursor; and U.S. Pat. No. 5,773,382 which discloses the use of removable pore modification agents in the preparation of the catalyst precursor to produce a catalyst precursor exhibiting a high proportion of large pores.

Thus, there are many different methods of producing and activating these catalysts, however the main active substance in all such catalysts is believed to be vanadyl pyrophosphate $(VO)_2P_2O_7$. This active substance is believed to be very sensitive to preparation conditions in terms of catalytic performance. In the past, improvements in catalytic performance have come from processing techniques including (1) dopant addition, such as Fe, Mo, Nb, Zr as promoters, for example, as described in U.S. Pat. No. 5,158,923; and (2) catalyst structure modification including catalyst shape and pore structure inside of catalyst particles, for example, as described in U.S. Pat. No. 5,168,090. Although these and other known techniques provide catalysts having appreciable activity and selectivity in the preparation of maleic anhydride, further improvements are desirable.

SUMMARY OF THE INVENTION

The present invention provides a process for preparing a VPO catalyst exhibiting improved catalyst performance which process comprises the steps of selecting an active VPO catalyst and contacting the active VPO catalyst with one or more fluids containing an organic solvent or a mixture of organic solvents.

In another embodiment, the process for preparing a VPO catalyst comprises the steps of selecting an active VPO catalyst and contacting the active VPO catalyst with one or more fluids containing an organic solvent or a mixture of organic solvents, each solvent having a dielectric constant of at least about 5 to about 55 when measured at a temperature of 20° C. to 25° C.

The invention also provides a VPO catalyst which is obtainable by a process for preparing the VPO catalyst according to this invention.

The invention further provides a process for preparing maleic anhydride comprising reacting a hydrocarbon having at least four carbons in a straight chain or a cyclic ring with a molecular oxygen-containing gas in the presence of the VPO catalyst of this invention.

DETAILED DESCRIPTION OF THE INVENTION

It has now been surprisingly found that catalysts comprising vanadium, phosphorus and oxygen (herein referred to as "VPO catalyst") having an improved catalyst performance in the preparation of maleic anhydride are prepared if, subsequent to activation by calcination of a VPO catalyst precursor, the active VPO catalyst is subjected to contacting with a fluid. This result is unexpected in view of the prior teachings which relate to VPO catalysts. Namely, one skilled in the art would expect that the contacting of an active VPO catalyst would lead to compounds absorbed at the solid surface which would adversely affect the performance of such catalyst.

As used herein, "calcination" generally embraces one or more gas and/or thermal treatment steps of a VPO catalyst precursor. The term "active" VPO catalyst thus refers to a catalyst that has been transformed from a VPO catalyst precursor by treatment with one or more gas and/or thermal treatment steps.

By the term "improved catalyst performance" it is meant there is an improvement in at least one of the VPO catalyst properties, which properties include yield, selectivity, conversion; yield, selectivity or conversion performance over time, and operability. For purposes of this invention, the term "yield" means the ratio of the moles of maleic anhydride obtained to the moles of hydrocarbon feedstock introduced into a reactor multiplied by 100, the term expressed as mol %. The term "selectivity" means the ratio of moles of maleic anhydride obtained to the moles of hydrocarbon feedstock reacted or converted multiplied by 100, the term expressed as mol %. The term "conversion" means the ratio of moles of hydrocarbon feedstock reacted to the moles of hydrocarbon introduced into a reactor multiplied by 100, the term expressed as mol %.

Accordingly, the present invention provides a process for preparing a VPO catalyst exhibiting improved catalyst performance which process comprises the steps of selecting an active VPO catalyst and contacting the active VPO catalyst with one or more fluids containing an organic solvent. The fluid may also comprise a mixture of organic solvents.

The active VPO catalyst selected for this invention may be any kind of known active VPO catalyst used for organic selective oxidation, particularly maleic anhydride production. Broadly described, the active VPO catalyst is prepared by reacting a vanadium-containing compound and a phosphorus-containing compound in an alcoholic medium to produce a VPO catalyst precursor, and activating the VPO catalyst precursor by calcination to convert a substantial fraction of the precursor composition to vanadyl pyrophosphate $(VO)_2P_2O_7$. Thus, in one embodiment, the active VPO catalyst may be a material having at least 70% $(VO)_2P_2O_7$ by weight based on the weight of the catalyst. In another embodiment, the active VPO catalyst may be a material having at least 90% $(VO)_2P_2O_7$ by weight based on the weight of the catalyst. A commercial example of an active VPO catalyst suitable for use in the present invention is sold under the trade name MARS V by Huntsman Corporation (The Woodlands, Tex.).

Vanadium-containing compounds in general are those containing pentavalent vanadium and include vanadium pentoxide or vanadium salts, such as ammonium metavanadate, vanadium oxytrihalides, and vanadium alkylcarboxylates. Among these compounds, vanadium pentoxide is preferred.

Phosphorus-containing compounds are preferably those that contain pentavalent phosphorus. Suitable phosphorus-containing compounds include phosphoric acid, phosphorus pentoxide, or phosphorus perhalides such as phosphorus pentachloride. Of these phosphorus-containing compounds, phosphoric acid and phosphorus pentoxide are preferred.

Promoter elements optionally may be added as solids, suspension of solids, or solutions to the catalyst precursor slurry either prior to or after the reaction of the vanadium and phosphorus-containing compounds has taken place. Promoter compounds that may serve as sources of the promoter elements include metal halides, metal alkoxides, and metal carboxylates. Of these compounds, metal carboxylates are preferred. Suitable carboxylates for metal salts include formate, acetate, propionate, butyrate, isobutyrate, pentanoate, hexanoate, heptanoate, octanoate, nonanoate, decanoate, and 2-ethylhexanoate. Of these carboxylates, 2-ethylhexanoate is preferred. In an embodiment, the promoter elements include Zr, Zn, Ti, Mn, Bi, Sn, Co, Ni, Mo, Nb, Cr, Fe, or combinations thereof.

The reaction between the vanadium and phosphorus-containing compounds may be carried out at any suitable temperature. In an embodiment, the reaction may be carried out at a temperature within a range of about 90° C. to about 120° C. and at a P/V ratio of 1.05 to 1.15.

During the course of carrying out the reaction, the VPO catalyst precursor forms and precipitates from the precursor slurry as a finely divided precipitate that may also contain the optional promoter elements. The VPO catalyst precursor may be recovered after cooling to below about 50° C. by conventional techniques well known to those skilled in the art, including filtration, centrifugation, and decantation.

The VPO catalyst precursor may then be dried at a relatively modest temperature of, for example, about 110° C. to about 150° C., and then subjected to "post dry" treatment (roasting) at a temperature in the range of about 200° C. to about 275° C.

The VPO catalyst precursor may then be directly converted to an active VPO catalyst by one or more gas and thermal treatments or it may first be compressed in a press or die to produce a slug and then subjected to gas and thermal treatment. The slug may be compressed into any desired shape or form, such as a cylinder, pyramid, cube, or sphere, to a measured density of between about 1.20 $g/cm^3$ to about 1.70 $g/cm^3$, preferably between about 1.40 $g/cm^3$ to about 1.60 $g/cm^3$. Binding and/or lubricating agents may be added, if desired, at amounts ranging from about 2% to about 6% by weight based on the total weight of the slug and may include starch, calcium stearate, stearic acid and graphite.

Converting the VPO catalyst precursor into the active VPO catalyst may take place in three controlled stages: (1) an initial heat-up stage, (2) a rapid heat-up stage, and (3) a maintenance/finishing stage.

In the initial heat-up stage, the VPO catalyst precursor is heated in an atmosphere selected from among air, steam, inert gas, and mixtures thereof, at any convenient heat-up rate. In general, suitable temperatures for the initial heat-up stage range from about 200° C. to about 300° C., alternatively a temperature from about 250° C. to about 275° C.

After the desired temperature has been achieved in the initial heat-up stage, the initially selected atmosphere (in the event it does not contain molecular oxygen and steam and/or has a different composition than that which is desired for the rapid heat-up stage) may be replaced by a molecular oxygen/steam-containing atmosphere, while maintaining the VPO catalyst precursor at the temperature achieved in the initial heat-up stage. Such atmosphere optionally may contain an inert gas and, as such, may be conveniently represented by the formula:

$$(O_2)_x(H_2O)_y(IG)_z$$

where IG is an inert gas and x, y, and z represent mole % (or volume %) of the $O_2$, $H_2O$, and IG components, respectively, in the molecular oxygen/steam-containing atmosphere; with x having a value greater than zero (0) mol %, but less than 100 mol %; y having a value greater than zero (0) mol %, but less than 100 mol %; and z having a value representing the balance of the molecular oxygen/steam-containing atmosphere. In an embodiment, the atmosphere may contain at least a portion of molecular oxygen and water (as steam). The presence of the inert gas in such atmosphere, as indicated by the formula, is optional. Nonlimiting examples of inert gases suitable for use in the molecular oxygen/steam-containing atmosphere include (molecular) nitrogen, helium, argon, and the like, with nitrogen generally being preferred.

Once the molecular oxygen/steam-containing atmosphere is provided, the VPO catalyst precursor is subjected to the rapid heat-up stage. In the rapid heat-up stage, the initial heat-up stage temperature may be increased at a programmed rate of from about 2° C. per minute (° C./min) to about 12° C./min, preferably from about 4° C./min to about 8° C./min, to a value effective to eliminate or remove the water of hydration. In general, a temperature from about 340° C. to about 450° C., alternatively at least about 350° C., alternatively from about 375° C. to about 425° C. is suitable.

Following the rapid heat-up stage, the VPO catalyst precursor is subjected to the maintenance/finishing stage. In the maintenance/finishing stage, the temperature may be adjusted to a value greater than 350° C. but less than 550° C., preferably from about 375° C. to about 450° C., most preferably from about 400° C. to about 425° C. The adjusted temperature is then maintained, first in the molecular oxygen/steam-containing atmosphere for a time effective to provide a vanadium oxidation state of from about +4.0 to about +4.5, and thereafter in a nonoxidizing, steam-containing atmosphere for a time effective to complete the VPO catalyst precursor to active VPO catalyst transformation. In a manner similar to the molecular oxygen/steam-containing atmosphere, the nonoxidizing, steam-containing atmosphere may also optionally contain an inert gas, with nitrogen generally being the preferred inert gas.

The active VPO catalyst may be in one or more different physical forms. In one embodiment, the active VPO catalyst is in the form of a powder having any particle size or particle sizes. In another embodiment, the active VPO catalyst is in the form of a shaped body. The shaped body may be any shape, including a cylinder, a cored cylinder, a sphere, a pellet, a trilobe, a quadrolobe, a bead, a ring, a tablet or an irregular shape. Examples of shaped bodies are described in U.S. Pat. No. 5,168,090, the contents of which are incorporated herein by reference.

The pore size inside of the active VPO catalyst shaped body may also be altered by a pore agent or a pore builder as described in U.S. Pat. Nos. 5,773,382 and 5,275,996, the contents of which are incorporated herein by reference.

For use in this invention, the active VPO catalyst is subjected to a series of contactings with one or more fluids. A series of contactings is herein understood to include a single contacting step and a combination of consecutive contacting steps which employ one or more fluids.

In accordance with this invention, the fluid comprises an organic solvent or mixture of organic solvents. In one embodiment, each organic solvent has a dielectric constant within a range of about 5 to about 55. In another embodiment, the organic solvents all have a dielectric constant within a range of about 10 to about 50. As used herein, the term "dielectric constant" is defined as a measure in the reduction of an electric field around a charged particle dissolved in the organic solvent, as compared to the electric field strength around the same particle in a vacuum. The dielectric constant thus is a measure of the polarity of the organic solvent. The higher the dielectric constant of a given solvent is, the lower the electrostatic forces, both attractive and repulsive, are between two ions dissolved in the solvent. For example, ions of opposite charge have a higher tendency to dissociate in a solvent with a high dielectric constant. In addition, the value of the dielectric constant depends on the temperature under which it is measured. Here, the dielectric constant of the organic solvent refers to the dielectric constant as measured at room temperature or a temperature of between 20° C. to 25° C.

Examples of organic solvents suitable for use include, but are not limited to, methanol, ethanol, n-propanol, n-butanol, isopropanol, isobutanol, acetonitrile, acetone, methyl ethyl ketone, DMF(N,N-dimethylformamide), Dimethyl sulfoxide, tetrafuran, ethylene glycol, propylene glycol, diethylene glycol, dipropylene glycol, 1,4-butanediol, glycerin and a mixture thereof.

Eligibly, the fluid comprises for the greater part the organic solvent or mixture of organic solvents. Thus, the organic solvent content of the fluid in one embodiment is preferably at least 90% by weight, more preferably at least 95% by weight, even more preferably at least 99% by weight, in particular, at least 99.9% by weight, and more in particular at least 99.99% by weight relative to the weight of the fluid. In one embodiment, the fluid consists of an organic solvent or a mixture organic solvents.

In another embodiment, the fluid may further comprise relative small quantities of other components, including, but not limited to, water, other organic matter, or inorganic matter.

The extent and type of contacting may be carried out in a continuous fashion or it may be carried out in a batch type of operation. There may be one contacting, but the number of contactings may also be two or three or more, for example up to five or ten. The contacting of the active VPO catalyst may be static or slow motion relative to the fluid(s). Thus, in one embodiment, the active VPO catalyst is kept static and the fluid is moved relative to the catalyst or vice versa. The relative motion speed may be at any range to allow the organic solvent in the fluid to diffuse into the active VPO catalyst body, but not at a speed which substantially damages the catalyst's pre-shaped body.

The quantity of fluid used in the contactings relative to the quantity of active VPO catalyst may be enough to cover the active VPO catalyst. The contacting may be carried out at any suitable temperature range, preferably within a range from room temperature (i.e. 20°-25° C.) to about 100° C. above the boiling point of the fluid, and more preferably from room temperature to the boiling point of the fluid. The contacting may be conducted in any pressure range, preferably from atmospheric pressure to 5 bars, more preferably from atmospheric pressure to 3 bars and most preferably at around 2 bars.

Contacting time may vary depending on the treatment conditions. The contacting time may be from a few minutes to a few weeks, whatever time is necessary to reach desired improved catalyst performance and as long as economic feasible. Thus, in one embodiment, the contacting time may range from a period of about 5 minutes to about 2 days. In another embodiment, the contacting time may range from a period of about 0.5 hours to about 12 hours.

After contacting the VPO catalyst, it may be desirable to perform a drying step. Drying of the contacted VPO catalyst may be performed at a certain temperature range under certain atmosphere. In one embodiment, drying may be carried out at a temperature ranging from about room temperature (i.e. 20° C. to 25° C.) to a temperature sufficient to remove the fluid from the VPO catalyst, for example, 300° C. In another embodiment, the temperature to remove the fluid from the VPO catalyst may be about 200° C. The temperature during drying may be held constant or varied over time. The drying may be carried out under a pressure range from about atmospheric pressure to vacuum with 10 mbar or with 50 mbar. The atmosphere may comprise air or inert gases or a mixture of air and inert gases. The inert gases may include nitrogen, helium, argon, carbon oxides, and mixtures thereof. In one embodiment, the atmosphere comprises air or nitrogen or a mixture thereof. The length of time of the drying step may vary from about 0.1 hour to a week or from about 0.5 hours to 3 days, or from about 1 hour to 12 hours depending on drying conditions.

The present invention also provides a process for preparing maleic anhydride which process comprises reacting a hydrocarbon having at least four (4) carbons in a straight chain or cyclic ring with a molecular oxygen-containing gas in the presence of the VPO catalyst of this invention. The process may be carried out as a batch process; however, it is more suitable to carry out the process as a continuous process. In one embodiment, the process is a gas phase process, wherein a gaseous feed comprising the reactants is contacted with the solid VPO catalyst. The solid VPO catalyst may be present in the form of a packed or fixed bed or in the form of a fluidized bed of catalyst particles. According to one embodiment, the VPO catalyst may be used in a fixed-bed reactor having a shaped body described above. In another embodiment, the VPO catalyst may be used in a fluid-bed or transport-bed reactor using comminuted catalyst particles having a particle size of less than about 300 microns.

In yet another embodiment, the VPO catalysts are used in tube-shell fixed-bed (tubular) with heat exchanger-type reactors. The tubes of such reactors may be constructed of iron, stainless steel, carbon steel, nickel, and/or glass and may vary in diameter from about 0.635 cm (0.25 inch) to about 5.08 cm (2 inches) and in length from about 15.24 cm (6 inches) to about 762 cm (25 feet) or more. It is desirable to have the surfaces of the reactors at relatively constant temperatures, and some medium to conduct heat from the reactors. Without being limited by theory, such medium aids in temperature control. Non-limiting examples of such media include Woods metal, molten sulfur, mercury, molten lead, and eutectic salt baths. A metal block reactor whereby the metal surrounding the tube acts as a temperature regulating body may also be used.

The hydrocarbon having at least four carbons in a straight chain or cyclic ring as used herein refers to a hydrocarbon containing not less than four carbon atoms in either a straight chain or in a cyclic ring. The hydrocarbon may be saturated, unsaturated, cyclic or aromatic. As an example, the saturated hydrocarbon n-butane is satisfactory, but iso-butane(2-methylpropane) is not satisfactory for conversion to maleic anhydride although its presence is not harmful. Typically, the hydrocarbon contains four to ten carbon atoms. Thus, in addition to n-butane, other suitable saturated hydrocarbons include the pentanes, the hexanes, the heptanes, the octanes, the nonanes, the decanes, and mixtures of any of these, with or without n-butane, so long as a hydrocarbon having at least four carbon atoms in a straight chain is present in the saturated hydrocarbon molecule.

The hydrocarbon having at least four carbons in a straight chain also includes unsaturated hydrocarbons. Unsaturated hydrocarbons suitable for use include the butenes such as 1-butene and 2-butene, 1,3-butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

In another embodiment, the hydrocarbon having at least four carbons in a cyclic ring is a cyclic hydrocarbon, for example, cyclopentane and cyclopentene, or an aromatic hydrocarbon, such as benzene.

Preferably, the hydrocarbon having at least four carbons in a straight chain or cyclic ring is selected from n-butane as the saturated hydrocarbon, 1-butene or 2-butene as the unsaturated hydrocarbons, and benzene as the aromatic hydrocarbons, with n-butane being most preferred of all feedstocks. It will be noted that the aforementioned feedstocks may not be pure substances but may be technical grade hydrocarbons. Moreover, a mixture of hydrocarbons having at least four carbon atoms in a straight chain or cyclic ring may also be used.

The reaction to convert the hydrocarbons to maleic anhydride may include contacting the hydrocarbons having at least four carbons in a straight chain or in a cyclic ring admixed with a molecular oxygen-containing gas (including molecular oxygen), such as air, synthetic air, molecular oxygen-enriched air, or "pure" oxygen (i.e. oxygen originating from air fractionation) with the VPO catalyst at elevated temperatures. In addition to the hydrocarbon and molecular oxygen-containing gas, other gases such as nitrogen and steam may be present or added to the reactant feed stream. In an embodiment, the hydrocarbon may be admixed with the molecular oxygen-containing gas, preferably air, at a concentration of from about one (1) mole percent to about ten (10) mole percent hydrocarbon and contacted with the VPO catalyst at a space velocity of about 100 $hr^{-1}$ to about 4,000 $hr^{-1}$ at a temperature between about 300° C. and about 600° C., preferably 1,000 $hr^{-1}$ to 3,000 $hr^{-1}$ and about 325° C. to about 450° C., to provide an excellent yield and selectivity to maleic anhydride.

The reaction may be conducted at atmospheric, super atmospheric, or subatmospheric pressure. In an embodiment, the reaction may be conducted at or near atmospheric pressure. Generally, pressures of from about $1.013 \times 10^{-2}$ kPa-gauge (14.7 psig, 1 atmosphere) to about $3.45 \times 10^{-2}$ kPa-gauge (50 psig) may be conveniently employed.

In an embodiment, the principal product from the oxidation of the aforementioned suitable feedstock is maleic anhydride, although small amounts of citraconic anhydride (methyl maleic anhydride) may also be produced when the feedstock is a hydrocarbon containing more than four carbon atoms. The maleic anhydride produced by using the VPO catalysts may be recovered by any suitable means. For example, maleic anhydride may be recovered by direct condensation or by absorption in suitable media with subsequent separation and purification of the maleic anhydride.

The recovered maleic anhydride may then be used in a variety of applications, for example, as a chemical intermediate in the synthesis of fumaric and tartaric acid and in certain agrochemical chemicals, dye intermediates and pharmaceuticals. It may also be used as a co-monomer for polyester and alkyd resins, as an ingredient in the manufacture of surface coatings, lubricant additives, plasticizers and as a preservative in oils and fats.

It is apparent that certain features of the invention, which are for clarity described herein in the context of separate embodiments, may also be provided in combination in a single embodiment. Conversely, features of the invention which are described in the context of a single embodiment may also be provided separately or in any suitable sub-combination.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

To further illustrate various illustrative embodiments of the present invention, the following non-limiting examples are provided.

EXAMPLES

VPO catalysts prepared according to this invention have been proven to be beneficial to maleic anhydride yield in a micro-reactor. Performance tests have demonstrated a yield increase from about 1% to about 5% depending on preparation conditions. The VPO catalyst according to this invention has also been loaded into a pilot scale reactor and has generated a >2.5% yield increase in maleic anhydride production as compared to a commercially available catalyst that has not been subjected to the process according to this invention.

Micro-Test General Description

Pre-shaped catalysts were tested for performance in a fixed bed maleic anhydride reactor at a standardized set of reaction conditions, including 2.0±0.2 mole % n-butane in air, about 15.0 psig inlet pressure, and 1500 GHSV. About 11.7 g of VPO catalyst was charged to a 1.092 cm inside diameter× 30.48 cm long (0.43 inch inside diameter by 1' long) reactor to provide a catalyst bed of approximately 15.24 cm (6") in length. The catalyst was run for a period of time from about 20 hours to about 130 hours, unless otherwise indicated, at the standardized performance test conditions prior to determining the yield. The maximum yield was determined for each catalyst when the catalyst was running at 85.0±0.2 mol % n-butane conversion.

In each test, in order to compare the maleic yield improvement, a commercially available active VPO catalyst was tested under the same conditions in parallel with the corresponding commercially available active VPO catalyst that has been subjected to the process in accordance with this invention The catalysts used in these tests had the shapes of either a trilobe or cored cylinder. Preliminary X-ray diffraction data of the example catalysts below show differences from the X-ray diffraction data of the commercially available catalyst.

Example 1

This example demonstrates improved catalyst performance through the use of ethanol as the organic solvent. 30 grams (g) of commercially available VPO catalyst (Mars V from Huntsman Corporation) was placed into a vessel and subjected to contacting. Contacting was carried out by immersing the catalyst in ethanol for 6 hours without stirring. The organic solvent was then drained from the vessel and the catalyst removed. The catalyst was allowed to air dry at room temperature for several hours then placed in an oven and further dried at 40° C. for 10 hours with $N_2$ as a purge gas. The VPO catalyst according to the present invention exhibited a Brunauer-Emmett-Teller (BET) surface area of 29.2 $m^2$/g as compared to the commercially available catalyst which exhibited a BET surface area of 21.2 $m^2$/g.

The catalysts were then performance tested at the conditions described above. The VPO catalyst contacted with ethanol generated a maleic anhydride yield of 56.4% in the micro-test, whereas the VPO catalyst that had not been contacted with ethanol generated a maleic anhydride yield of 55.2% in the micro test.

Example 2

This example demonstrates improved catalyst performance through the use of ethylene glycol as the organic solvent. A thermal bath with fresh ethylene glycol (EG) was heated to 100° C. 100 g of commercially available VPO catalyst was placed in a vessel having holes through which the organic solvent could contact the catalyst in the container. The catalyst was then subjected to contacting by immersing the vessel into the bath of EG. The catalyst was contacted with EG for 3 hours then removed from the bath, and placed into a preheated oven at 100° C. and dried for 3 hours with nitrogen purge. The temperature of the oven was then ramped up to a temperature of 190° C. at 2° C./min and the catalyst was further dried for 3 hours at this temperature. The temperature of the oven was then ramped up further to 250° C. at 2° C./min and the catalyst was dried at this temperature for 3 hours.

Performance testing at the conditions described above demonstrated that the VPO catalyst contacted with EG generated a maleic anhydride yield of 60.5% in the micro-test. In comparison, the VPO catalyst that had not been contacted generated a maleic anhydride yield of 56.6% in the micro test.

Example 3

This example demonstrates improved catalyst performance using acetonitrile as the organic solvent. 30 g of commercially available VPO catalyst was placed into a vessel. Contacting was carried out by immersing the catalyst in acetonitrile. The catalyst was contacted with acetonitrile for 8 hours without stirring. The organic solvent was then drained from the vessel and the catalyst removed. The catalyst was allowed to air dry at room temperature for several hours then placed in an oven and further dried at 50° C. for 1 hour, 60° C. for 1 hour and finally 70° C. for 6 hours with $N_2$ as a purge gas.

The VPO catalyst according to the present invention exhibited a BET surface area of 35.5 $m^2$/g, which was much higher than the commercially available catalyst which exhibited a BET surface area of 21.4 $m^2$/g.

The catalysts were then performance tested at the conditions described above. The VPO catalyst contacted with acetonitrile generated a maleic anhydride yield of 55.2% in the micro-test, whereas the VPO catalyst that had not been contacted with acetonitrile generated a maleic anhydride yield of 53.8% in the micro test.

Example 4

This example demonstrates improved catalyst performance using DMF (N,N-dimethylformamide, >99.8%) as the organic solvent. 30 g of commercially available VPO catalyst was placed in a vessel. Contacting was carried out by immersing the catalyst in DMF for 4 hours without stirring. The organic solvent was then drained from the vessel and the catalyst removed. The catalyst was allowed to air dry at room temperature for several hours then placed in an oven and further dried at 120° C. for 2 hours, and 140° C. for 6 hours with $N_2$ as a purge. The VPO catalyst according to the present invention exhibited a BET surface area of 26.3 $m^2$/g as compared to the original commercially available catalyst which exhibited a BET surface area of 21.2 $m^2$/g The catalysts were then performance tested at the conditions described above. The VPO catalyst contacted with DMF generated a maleic anhydride yield of 53.58% in the micro-test, whereas the VPO catalyst that had not been contacted with DMF generated a maleic anhydride yield of 52.6% in the micro test.

Example 5

This example demonstrates improved catalyst performance using propylene glycol (PG) as the organic solvent. 80 g of commercially available VPO catalyst was placed in a vessel having holes in the wall. Contacting was carried out by slowly immersing the vessel containing the catalyst into a preheated thermal bath (100° C.) containing PG. The catalyst was contacted for 6 hours and removed from the bath and placed into a preheated oven (100° C.) with nitrogen purge. The temperature of the oven was then ramped up to a temperature of 180° C. at 2° C./min, and the catalyst was dried for 1 hour. The temperature of the oven was then ramped up further to a temperature of 190° C. at 3° C./min, and the catalyst was dried for 3 hours. The temperature of the oven was ramped up again to 250° C. at 3° C./min and the catalyst was dried for 3 hours. The VPO catalyst according to the present invention exhibited a BET surface area of 36 $m^2/g$ as compared to the commercially available catalyst which exhibited a BET surface area of 20.8 $m^2/g$. Performance testing of the two catalysts demonstrated a maleic anhydride yield increase of 3 percentage points for the catalyst according to the present invention as compared to the commercially available VPO catalyst in micro tests.

Example 6

This example demonstrates improved catalyst performance using 1,4-butanediol as the organic solvent. 80 g of commercially available VPO catalyst with Mo as a promoter was placed in a vessel having holes in the wall. Contacting was carried out by slowly immersing the vessel containing the catalyst into a preheated thermal bath (100° C.) containing 1,4-butanediol. The catalyst was contacted with 1,4-butanediol for 4 hours and removed from the bath and placed into a preheated oven (100° C.) with nitrogen purge. The temperature of the oven was then ramped up to a temperature of 220° C. at 2° C./min, and the catalyst was dried for 1 hour. The temperature of the oven was then ramped up further to a temperature of 230° C. at 2° C./min, and the catalyst was dried for 3 hours. The temperature of the oven was ramped up again to 250° C. at 3° C./min and the catalyst was dried for 3 hours. The VPO catalyst according to the present invention exhibited a BET surface area of 28 $m^2/g$ as compared to the original commercially available catalyst which exhibited a BET surface area of 19.8 $m^2/g$. Performance testing of the two catalysts demonstrated a maleic anhydride yield increase of 3 percentage points for the catalyst according to the present invention as compared to the commercially available catalyst in micro tests.

Example 7

This example demonstrates improved catalyst performance by a VPO catalyst according to the present invention (a commercially available VPO catalyst contacted with ethylene glycol (EG) as described in Example 2) with performance testing conducted in a pilot scale reactor. The pilot scale reactor was 20 feet long and one inch I.D. and loaded with 6 inches of alumina at bottom, then 212 inches of VPO catalyst and about 34 inches alumina on the top. Space velocity was controlled at 1820 $m^3/m^3$ h, and n-butane feed concentration at 2.0±0.2%. Maleic anhydride yield maintained at around 58.6% at n-butane conversion of 85% after 500 hours on stream using the catalyst according to the present invention, which was 1.6% higher than the maleic anhydride yield maintained when using the commercially available catalyst that had not been contacted with EG.

Although the present invention and its advantages have been described in detail, it should be understood that various changes, substitutions and alterations may be made herein without departing from the spirit and scope of the invention as defined by the appended claims.

What is claimed is:
1. A process for preparing a VPO catalyst comprising the steps of:
   (i) adding a pore agent to a VPO catalyst precursor;
   (ii) thermally treating the VPO catalyst precursor to remove the pore agent and form an active VPO catalyst; and
   (iii) contacting the active VPO catalyst with one or more fluids comprising an organic solvent.
2. The process according to claim 1 wherein the organic solvent has a dielectric constant within a range of about 5 to about 55 when measured at a temperature of 20° C. to 25° C.
3. The process according to claim 1 wherein the organic solvent has a dielectric constant within a range of about 10 to about 50 when measured at a temperature of 20° C. to 25° C.
4. The process according to claim 1 wherein the organic solvent is selected from the group consisting of methanol, ethanol, n-propanol, n-butanol, isopropanol, isobutanol, acetonitrile, acetone, methyl ethyl ketone, DMF, dimethyly sulfoxide, tetrafuran, ethylene glycol, propylene glycol, diethylene glycol, dipropylene glycol, 1,4-butanediol, glycerin and a mixture thereof.
5. The process according to claim 1 wherein the active VPO catalyst comprises at least 90% by weight $(VO)_2P_2O_7$ based on the weight of the catalyst.
6. The process according to claim 1 wherein the active VPO catalyst further comprises a promoter.
7. The process according to claim 1 wherein contacting is carried out at a temperature within a range from room temperature to 100° C. above the boiling point of the fluid.
8. The process according to claim 7 wherein contacting is carried out at a temperature within a range from room temperature to the boiling point of the fluid.
9. The process according to claim 1 wherein contacting is carried out a pressure ranging from atmospheric pressure to 5 bars.
10. The process according to claim 9 wherein contacting is carried out a pressure ranging from atmospheric pressure to 3 bars.
11. The process according to claim 1 further comprising drying the contacted VPO catalyst.
12. The process according to claim 11 wherein drying is carried out a temperature ranging from room temperature to 300° C.
13. The process according to claim 11 wherein drying is carried out in an atmosphere comprising air, an inert gas or a mixture thereof.
14. A process for preparing maleic anhydride comprising reacting a hydrocarbon having at least four carbons in a straight chain with a molecular oxygen-containing gas in the presence of a VPO catalyst prepared by a process comprising the steps of:
   (i) adding a pore agent to a VPO catalyst precursor;
   (ii) thermally treating the VPO catalyst precursor to remove the pore agent and form an active VPO catalyst; and
   (iii) contacting the active VPO catalyst with one or more fluids comprising an organic solvent.

15. The process according to claim 14 wherein the organic solvent has a dielectric constant within a range of about 5 to about 55 when measured at a temperature of 20° C. to 25° C.

16. The process according to claim 14 wherein the hydrocarbon is selected from the group consisting of a saturated hydrocarbon, an unsaturated hydrocarbon, a cyclic hydrocarbon, an aromatic hydrocarbon and a mixture thereof.

17. The process according to claim 14 wherein the hydrocarbon is selected from the group consisting of n-butane, 1-butene, 2-butene, benzene and a mixture thereof.

18. The process according to claim 14 wherein the reaction occurs at a temperature ranging from 300° C. to 600° C., a space velocity ranging from about 100 $hr^{-1}$ to about 4000 $hr^{-1}$, and a pressure ranging from subatmospheric pressure to superatmospheric pressure.

19. The process according to claim 14 wherein the reaction occurs at a temperature ranging from about 325° C. to 450° C., a space velocity ranging from about 1000 $hr^{-1}$ to 3000 $hr^{-1}$ and a pressure ranging from about $1.013 \times 10^{-2}$ kPa-gauge to about $3.45 \times 10^{-2}$ kPa-gauge.

\* \* \* \* \*